United States Patent
Van Wyck et al.

(10) Patent No.: US 10,516,762 B2
(45) Date of Patent: Dec. 24, 2019

(54) SYSTEM FOR REMOTELY RUNNING A SERVICE PROGRAM

(71) Applicant: Zillion Group, Inc., Norwalk, CT (US)

(72) Inventors: William Van Wyck, Darien, CT (US); Theresa Biasi, Shelton, WI (US); Kelly Jura, Seymour, CT (US); Michelle Stevens, Stamford, CT (US); Anuja Ketan, Oxford, CT (US)

(73) Assignee: Zillion Group, Inc., Norwalk, CT (US)

( * ) Notice: Subject to any disclaimer, the term of this patent is extended or adjusted under 35 U.S.C. 154(b) by 150 days.

(21) Appl. No.: 15/584,671

(22) Filed: May 2, 2017

(65) Prior Publication Data

US 2017/0324865 A1 Nov. 9, 2017

Related U.S. Application Data

(60) Provisional application No. 62/331,037, filed on May 3, 2016.

(51) Int. Cl.
*G08C 19/16* (2006.01)
*H04L 29/08* (2006.01)
(Continued)

(52) U.S. Cl.
CPC ............ *H04L 67/34* (2013.01); *A61B 5/0022* (2013.01); *A61B 5/1118* (2013.01);
(Continued)

(58) Field of Classification Search
CPC ............. H04M 3/487; H04M 3/42144; H04M 3/42127; G16H 40/67; G06F 19/00;
(Continued)

(56) References Cited

U.S. PATENT DOCUMENTS 8,732,739 B2  5/2014  Sillerman
2012/0060156 A1  3/2012  Keys
(Continued)

FOREIGN PATENT DOCUMENTS

WO  2009056148 A2  5/2009
WO  2012099661 A3  7/2012
(Continued)

OTHER PUBLICATIONS

Taylor Soper (https://www.geekwire.com/author/taylor-soper/) on Aug. 21, 2013; Microsoft awarding free Surface tablets with new ad-free "Bing for Schools" Initiative—12 pages.
(Continued)

*Primary Examiner* — Tanmay K Shah
(74) *Attorney, Agent, or Firm* — Boyle Fredrickson, S.C.

(57) ABSTRACT

A system is provided in which portable electronic devices may be provided to people for accessing services in mass quantities. Each portable electronic device, which may be a tablet, may be configured in advance with one or more service programs and an authentication process. The tablet may also include cellular data access and/or paired peripheral devices. Such pre-configuration may provide subsequent ease of use and/or guarantee compatibility with a provider's server. A device control module on the tablet may communicate with a device manager on a server to monitor progress of the service program. If data values associated with the service program, such as measurements and/or transferred content, fail to meet a threshold within a period of time, the device control module may implement an action on the device to encourage the user, such as triggering repetitive alerts, disabling cellular access, disabling system applications, and the like.

17 Claims, 4 Drawing Sheets

(51) Int. Cl.
  *H04M 3/42* (2006.01)
  *A61B 5/11* (2006.01)
  *A61B 5/00* (2006.01)
  *A61B 5/145* (2006.01)
  *G06F 19/00* (2018.01)
  *G16H 40/67* (2018.01)

(52) U.S. Cl.
  CPC .......... *A61B 5/14532* (2013.01); *G06F 19/00* (2013.01); *G16H 40/67* (2018.01); *H04M 3/42144* (2013.01); *H04M 3/42178* (2013.01); *H04L 67/26* (2013.01)

(58) Field of Classification Search
  CPC . A61B 5/14532; A61B 5/0022; A61B 5/1118; H04L 67/34; H04L 67/26
  USPC ...................................... 340/12.25
  See application file for complete search history.

(56) References Cited

U.S. PATENT DOCUMENTS

| | | | | |
|---|---|---|---|---|
| 2013/0145390 A1* | 6/2013 | Sillerman | ........ | H04N 21/42203 725/18 |
| 2014/0108543 A1 | 4/2014 | Windust | | |
| 2014/0214446 A1* | 7/2014 | Nusbaum | ............... | G09B 19/00 705/2 |
| 2014/0316616 A1* | 10/2014 | Kugelmass | ............ | G05D 1/101 701/8 |
| 2015/0188889 A1* | 7/2015 | Lawson | .............. | H04L 63/0272 726/15 |
| 2015/0312422 A1* | 10/2015 | Leemet | ................ | H04L 41/082 455/406 |

FOREIGN PATENT DOCUMENTS

| | | |
|---|---|---|
| WO | 2013009446 A1 | 1/2013 |
| WO | 2013052729 A2 | 11/2013 |
| WO | 2016022440 A1 | 2/2016 |

OTHER PUBLICATIONS

Tingxin Yan and Jing Yang (http://www.hotmobile.org/2013/papers/posters/Hotmobile_poster_Yan.pdf)—1 page.

C Spire (https://www.statewidefcu.org/sites/www/Uploads/images/Introducing%20the%20FREE%20TABLET.pdf); Introducing The FREE Tablet—1 page.

David K. Vawdrey, Lauren G. Wilcox; Sarah A. Collins; Suzanne Bakken: Steve Feiner, Aurelia Boyer and Susan W. Restaino (http://www.ncbi.nlm.nih.gov/pmc/articles/PMC3243172/) on Oct. 22, 2011; A Tablet Computer Application for Patients to Participate in Their Hospital Care—9 pages.

* cited by examiner

SYSTEM FOR REMOTELY RUNNING A SERVICE PROGRAM

CROSS-REFERENCE TO RELATED APPLICATION

This application claims priority to U.S. Provisional Patent Application No. 62/331,037, entitled "System for Remotely Running a Service Program," filed on May 3, 2016, which is herein incorporated by reference.

FIELD OF THE INVENTION

The present invention is directed to the field of service programs, such as for health or education services, and more particularly, to a portable electronic device which may run a service program and implement an action on the device when data values received by the service program fail to meet a threshold.

BACKGROUND OF THE INVENTION

Mechanisms for providing remote services to people are continuing to grow rapidly. For example, while patients of health services were once required to a physically visit a doctor's office or health care facility to receive treatment, such patients may now receive many of the same treatments remotely using various technologies. In fact, a patient can now use a personal computer, tablet or smartphone with an Internet connection to schedule appointments, communicate directly with health services professionals, manage medical information, and the like. However, numerous technical and social barriers remain for taking widespread advantage of these efficiencies. For example, if a user's personal computer is not installed with the correct Internet browser, version and/or software plug-ins, the user may not be able to access a service provider's website and/or content. Moreover, many users still lack a personal computer, tablet or smartphone altogether, or the skill which may be necessary to configure such equipment, thereby requiring them to continue to receive most of their services in person or by telephone.

SUMMARY OF THE INVENTION

The present invention provides a system in which portable electronic devices may be provided to people for accessing services in mass quantities. Each portable electronic device, which may be a tablet, may be configured in advance with one or more service programs and an authentication process. The tablet may also include cellular data access and/or paired peripheral devices. Such pre-configuration may provide subsequent ease of use and/or guarantee compatibility with a provider's server. A device control module on the tablet may communicate with a device manager on a server to monitor progress of the service program. If data values associated with the service program, such as measurements and/or transferred content, fail to meet a threshold within a period of time, the device control module may implement an action on the device to encourage the user, such as triggering repetitive alerts, disabling cellular access, disabling system applications, and the like.

Accordingly, aspects of the invention may provide a program delivery device which may provide an incentive for users to engage with a service program. The program delivery device may remove technical barriers to remote service delivery, such as for healthcare or education. Such a device may be completely set up for a user prior to delivery. In some aspects, the device may be preloaded with one or more service programs, relevant applications, user authentication/validation data, preset music channels, and/or other service related content, such as videos and/or audio for exercise or relaxation as part of a health program or for studies as part of an education program. In addition, one or more peripheral monitoring devices may be registered and connected (such as via Bluetooth) in advance and provided with the device. Program configurations may be set and locked, including with alerts, notifications and/or reminders, which may help maintain engagement and adherence to the program plan. The device may then be shipped to a particular user for when the user is ready to begin the program, such as following a surgery or rehabilitation.

In some aspects, the device may also be branded for a particular service provider. The device may be configured to be procedure specific (such as for any patient undergoing a common treatment plan or student undergoing a common education plan) or may be user specific (such as for a particular patient undergoing one or more treatment plans or a particular student undergoing one or more education plans). The device may be further configured according to the needs of a particular user, such as being preset to a large font for patients undergoing eye procedures, being provided with clamps for a walker or treadmill for patients undergoing physical therapy, being provided with a special stylus for patients undergoing peripheral neuropathy in the hands, and so forth.

Cases may be provided with the device for particular groups of users, such as cases which may be childproof, elder friendly, impact resistant, brightly colored, and the like. Such cases may also have an integrated stand for attending live video sessions with health professionals or teachers.

Upon completion of the one or more service programs, such devices can be returned, refurbished and reused for another user. Alternatively, aforementioned control of such devices may be removed to allow user to permanently keep the devices as a final incentive. Devices may communicate via a wireless local area network (WLAN), cellular data interface and/or Bluetooth interface. Having a device with a cellular data interface and data plan may serve as a function providing significant incentive for user to receive the device and participate in the service program in order to keep the device and retain the data plan. In one aspect, if the cellular interface and/or data plan is disabled for lack of participation, users may continue to use the device via the WLAN interface to potentially regain the cellular interface and/or data plan.

The device may be used to generally browse the Internet. However, the device control module may limit an amount of Internet access which may occur in a given period of time. Also, the device control module may filter adult content and/or data intensive downloads, such as movies, from being received. Additional data download capacity may be provided as reward for active program participation based on results or activity, such as according to data values received. Individual device data usage may be monitored and adjusted as needed. In addition, the device may be configured to provide a "thumbnail" view of the service program even while executing other applications.

In some cases, cost of the device may be included, or at least offset, by payment from a grantor or insurer. This may allow technically challenged users to have easier access, for example, to live video sessions from anywhere. This may also allow providers to have control over the user's device environment, such as the Operating System (OS) version, user experience, colors, sounds, installed applications and content, and so forth. The device may also include an application operable to include family and friends via video. In some cases, a single entity could provide an logistics for setup (configuration in advance), fulfillment to users and returns of the device to provide a convenient "out of box" experience in which users may simply take the device out of box, turn it on and be ready to provide data values in the service program.

In one aspect, software may be utilized to manage the device. The software may allow monitoring of the service program and/or access to the device, including disabling the device remotely if the service program is not being followed (such as not launching the service program or not entering data values). This may provide an incentive to continue with the program in order to keep the device. Personal use of the device may be allowed, and the device may be provided free of charge with a data plan. The device may provide two-way interactive video and content delivery which may advantageously scale care outside of health facilities, schools, and the like. Health programs and content may be clinically-managed with live video support, including for behavioral changes. Programs may be configurable to support preventive, chronic and procedural care at scale, including with one-click ordering for supplies. The device may also implement security and communications protocols for health programs which are compliant with the United States Health Insurance Portability and Accountability Act (HIPAA).

In another aspect, the device may be configured to push sponsored coupons to the device. Also, if devices are to be returned, participation in the service program may provide a way for users to earn "points" in which a certain number of points may allow the user to keep the device. Also, non-program related games and/or content may be pushed to the device from the server as a way to keep the user continuously engaged with the device.

Specifically, then, one aspect of the invention may provide a portable electronic device for running a service program. The portable electronic device may include a wireless communications interface; a touchscreen interface; and a processor executing a program stored in a non-transient medium. The portable electronic device may be operable to: (a) execute a service program configured to receive multiple data values; (b) communicate the multiple data values to a server via the wireless communications interface; and (c) execute a device control module in communication with the server. The device control module may be configured to implement an action on the portable electronic device when the multiple data values fail to meet a threshold.

Another aspect of the invention may provide a system for running a service program. The system may include a server having a server communications interface and a processor executing a program stored in a non-transient medium operable to execute a device manager. The system may also include a portable electronic device having: a wireless communications interface; a touchscreen interface; and a processor executing, a program stored in a non-transient medium. The portable electronic device may be operable to: (a) execute a service program configured to receive multiple data values; (b) communicate the multiple data values to the server via the wireless communications interface; and (c) execute a device control module in communication with the device manager of the server. The device control module may be configured to implement an action on the portable electronic device upon receiving a command from the device manager. The device manager may send the command to the device control module when the multiple data values fail to meet a threshold.

These and other features and advantages of the invention will become apparent to those skilled in the art from the following detailed description and the accompanying drawings. It should be understood, however, that the detailed description and specific examples, while indicating preferred embodiments of the present invention, are given by way of illustration and not of limitation. Many changes and modifications may be made within the scope of the present invention without departing from the spirit thereof, and the invention includes all such modifications.

BRIEF DESCRIPTION OF THE DRAWINGS

Preferred exemplary embodiments of the invention are illustrated in the accompanying drawings in which like reference numerals represent like parts throughout, and in which.

DETAILED DESCRIPTION OF THE PREFERRED EMBODIMENT

Figure 1:
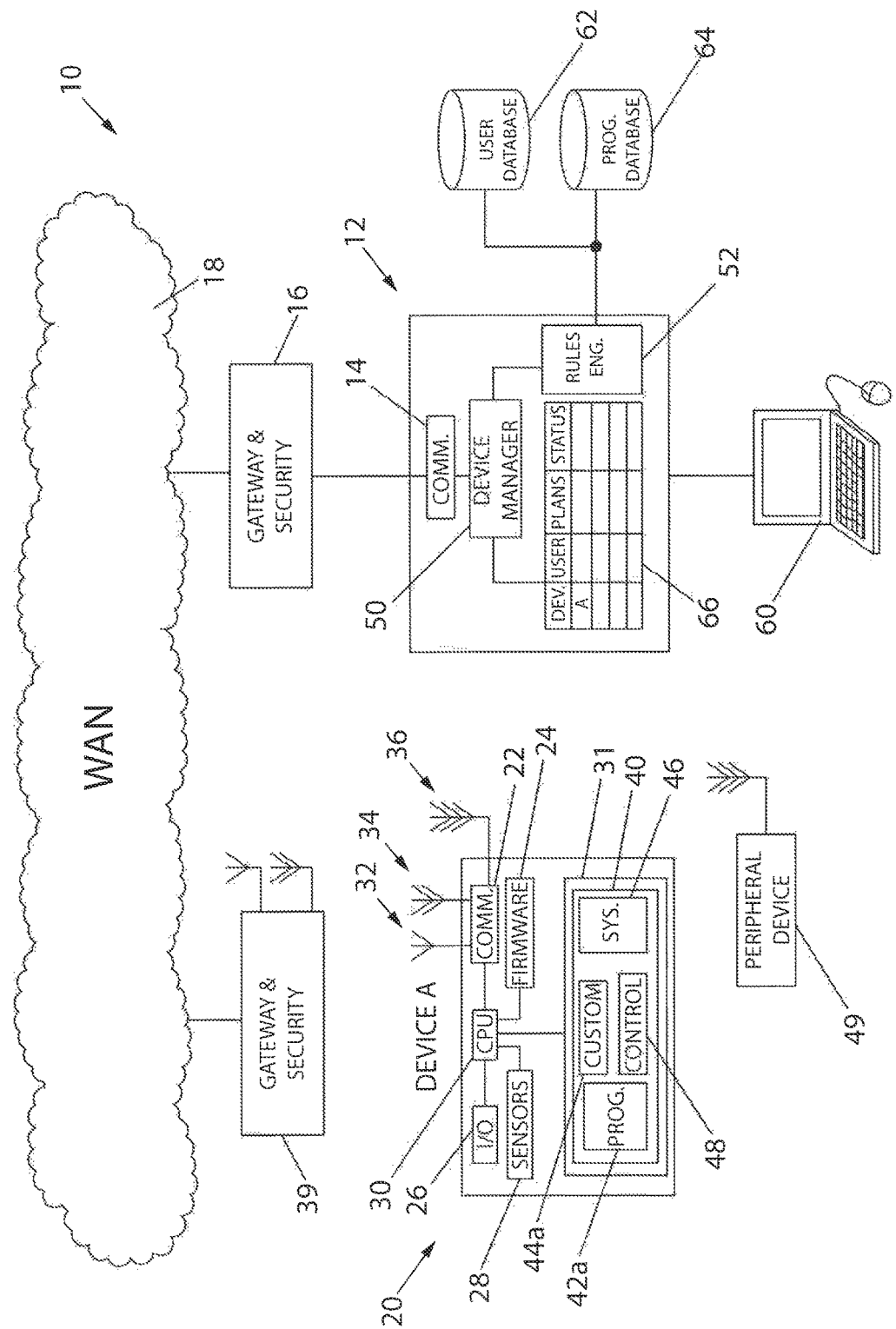
FIG. 1 is a diagram providing a system for remotely running a service program in accordance with an embodiment of the invention.

Referring now to FIG. 1, a system 10 is provided for remotely running a service program in accordance with an embodiment of the invention. The system 10 may include a server 12 having a server communications interface 14 which may be provide wired or wireless communications and a processor executing a program stored in a non-transient medium. The server 12 may communicate with a first access device 16, which may be a wired or wireless gateway or router implementing firewall and/or other security functions known in the art, via the server communications interface 14. Accordingly, the server 12 may communicate via a Wide Area Network (WAN) 18 such as the Internet.

The system 10 may also include one or more portable electronic devices 20, which may be implemented by tablet computers, smartphones and the like. A portable electronic device 20, labeled "Device A" in FIG. 1, is illustrated by way of example. The device 20 may include a communications chipset 22, a firmware 24, an input/output (I/O) system 26, multiple sensors 28, a processor 30, and a non-transient memory 31 which may be a flash memory, among other things.

The communications ellipse 22 may include: a first wireless communications interface 32, which may be a cellular data interface for implementing mobile telecommunications with a WAN, such as according to fourth generation (4G) and/or Long-Term Evolution (LTE) technologies; a second wireless communications interface 34, which may be a wireless local area network (WLAN) interface implementing local area network communications, such as according to wireless Ethernet technologies; and/or a third wireless communications interface 36, which may be a short distance interface for implementing data communications, such as according to Bluetooth; among others. The device 20 may communicate with a second access device 39, which may be a wireless gateway or router implementing firewall and/or other security functions known in the art, via the first wireless communications interface 32 (when enabled) and/ or the second wireless communications interface 34. Accordingly, the device 20 may communicate via the WAN 18 and, in turn, the server 12.

The firmware 24, stored in flash memory, may enable special uses, functions or customizations of the device 20. Accordingly, the firmware 24 may be configured in advance (before delivery to the user) and may be updated from time to time, such as upon a remote command by the server 12. The I/O system 26 may include, for example, a touchscreen interface, a home button, mute and/or volume control buttons, a speaker, a mechanical device for producing vibrations, and/or a charging/data connector. The sensors 28 may include, for example, a camera, microphone, accelerometer, gyroscope, digital compass, proximity sensor, touch ID fingerprint reader, and/or ambient light detector. The memory 31 may be, for example, a large capacity flash memory for general storage and data processing, such as on the order of 64 Gigabytes (GB).

The processor 30 may execute an Operating System (OS) 40, running in the memory 31, which may be for example, an Android or other mobile OS. One or more service programs 42, such as a health or education program, may be configured in advance to execute on the device 20 in the environment of the OS 40. Each program 42 may be preloaded on the device according to the user's specific needs, along with custom content 44 which may relate to the program 42 and the user's needs. For example, a first program 42a may be a diabetes health program installed for a user that is a diabetes patient, along with first custom content 44a which may include one or more educational videos about diabetes. In addition, a second program 42b (not shown) may be a catheter health program installed on the same device 20 for the same user also having a catheter, along with second custom content 44b (not shown) which may include one or more articles about safe usage of catheters. Each program 42 may be configured to receive multiple data values, such as via the I/O system 26 and/or the communications chipset 22, and may communicate such data values to the server 12.

In addition, multiple system applications 46 may be configured to execute on the device 20 in the environment of the OS 40. Such system applications 46 may provide general functionality for the device 20 which may be expected for a tablet, such as an Internet browser, instant messaging service, electronic mail service, music player, calculator, clock, calendar, camera control, application store and/or games.

The processor 30 may further execute a device control module 48 in the memory 31. The device control module 48 may be configured to provide control over the device 20, and more particularly, the program 42, custom content 44 and/or system applications 46. The device control module 48 may also be in communication with a device manager 50 being executed by the processor on the server 12. Accordingly, the device control module 48 may implement an action on the device 20 according to: (i) determining a requirement on the device 20 as being met, and/or (ii) receiving a command from the server 12 which has determined a requirement for the device 20 as being met. For example, in a first instance, the device control module 48 may be configured to implement an action on the device 20, such as to trigger an alarm or disable a function, upon determining that collection and/or communication of data values associated with the program 42 fails to meet a threshold. Also, in a second instance, the device control module 48 may be configured to implement an action on the device 20, such as to trigger an alarm or disable a function, upon receiving a command from the server 12 which has determined that collection and/or communication of data values associated with the program 42 fails to meet a threshold (which may be a minimum amount of data per given period of time).

Thresholds for implementing actions and types of actions may also be configured in advance according to various factors, including abilities of the user, nature and length of the service programs, cost and features of the equipment, goals of the provider, and the like. In one aspect, thresholds for implementing actions and the types of actions may be implemented by a rules engine 52 executing by the processor on the server 12. For example, the rules engine 52 may determine that for devices 20 running the first program 42a (diabetes program) in which data values may correspond to glucose measurements, such measurements should be made at least daily, and failing to receive measurements from the device 20 by a threshold of at least five measurements in one week may result in implementing a first type of action in which a visual alert (pop-up screen) may be displayed to the touchscreen interface. The rules engine 52 may further provide for repeating this determination on a weekly basis, and upon determining a failure to receive such measurements according to the threshold for three consecutive weeks, implementing a second type of action in which access to a system application 38, such as the Internet browser, may be to disable.

It will be appreciated that a variety of thresholds and/or actions may be implemented according to aspects of the invention. For example, a threshold may correspond to a minimum number of data values expected for a program 42 within a given period of time, or a minimum amount of data transferred for a program 42 and/or custom content 44 within a given period of time, and so forth. Also, types of actions may correspond to disabling cellular access, disabling system applications, triggering repetitive alerts to the touchscreen interface, speakers, and/or vibration system, and the like. Such variations are deemed within the scope of the invention.

The system 10 may also include one or more peripheral devices 49. Each peripheral device 49 may be configured in advance to communicate with the device 20, such as via the third wireless communications interface (Bluetooth). Peripheral device 49 may include, for example, wearable activity trackers, glucose monitors, blood pressure monitors, temperature sensors, and the like. Accordingly, the device 20 may be paired with a peripheral device 49 so that the device 20 may receive data from the peripheral device 49 for the program 42 when used by a user.

In addition, in the system 10, the server 12 may be in wired or wireless communication with a workstation 60 or similar terminal which may provide a display, keyboard, mouse and/or other I/O. The workstation 60 may be used by a provider for monitoring operation of the system 10.

The server 12 may also be in communication with a first data structure 62, which may provide patient, student or other user information, and/or a second data structure 64, which may provide service program and/or content information. Each of the first and second data structure 62 and 64, respectively, may be updated from time to time via the WAN 18. The first data structure 62 may include user information which may be provided by the user and/or a service provider and which may be consistent, for example, with an Electronic Medical Record (EMR) or Student Record. Accordingly, the first data structure 62 may be used by the server 12 to determine information about the user for configuring a device 20 for the user in advance, such as health or education needs for selecting a health or education program, personally identifiable information for enabling a secure activation and authentication process by the user, and so forth. The second data structure 64 may include various programs 42 and related custom content 44 which may be drawn upon for configuring the device 20 based on the user's health needs.

The server 12 may also include a tracking system 66, which may be a look up table for example, for monitoring and managing multiple devices 20 in the system 10. For example, a first row in the tracking system 66 may correspond to a particular device 20 via a unique identifier, such as the device "A," which may be Media Access Control (MAC) address or static Internet Protocol (IP) address of the device 20 in the system 10. Subsequent entries in the row may correspond, for example, to the name, address, telephone number and/or email address of the user that has been assigned the device 20, the programs 42 or plans being implemented on the device 20 for the user, and/or status information for the device 20, which may continuously track data values of the device 20 for comparison to thresholds, current states of the device 20 and/or pending actions.

Figure 2:
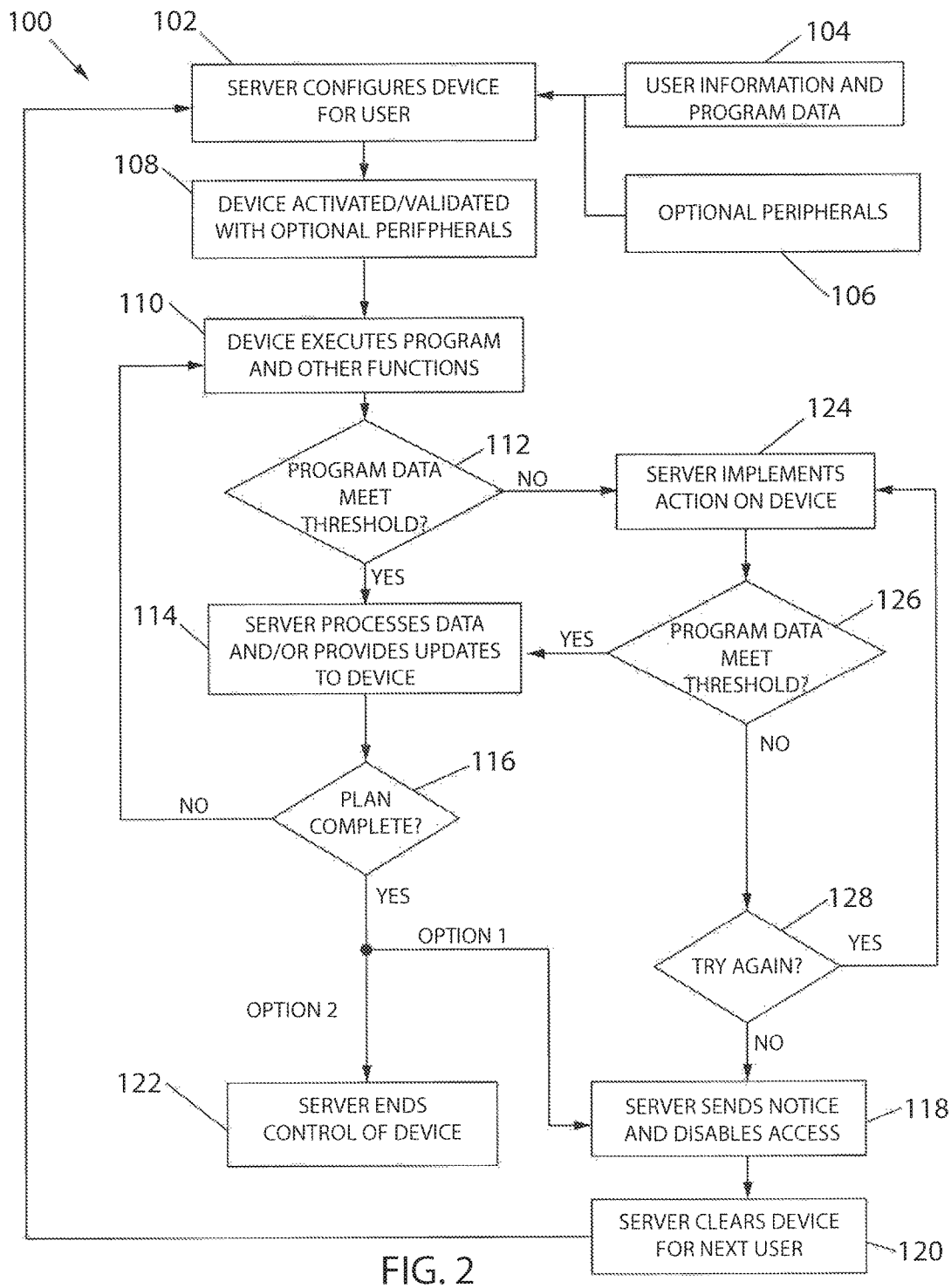
FIG. 2 is a process flow which may be implemented in the system of FIG. 1.

Referring now to FIG. 2, a process flow 100 is provided which may be implemented in the system of FIG. 1. At step 102, the server 12 may configure a portable electronic device 20 in advance for a particular user undergoing a program 42. Configuring the device 20 may include retrieving user information, service program data and/or custom content at step 104, such as from the first and second data structures 62 and 64, respectively, and programming the device 20 accordingly. The server 12 may essentially customize the device 20 for the user, including with a program 42 as part of a health plan, and may optionally install authentication information, such as a date of birth, which the user may be required to enter in order to activate the device 20. At step 106, configuring the device 20 may also include selecting and pairing one or more peripheral devices 49 with the device 20 and verifying correct operation. Peripheral devices 49 may be selected and paired depending on the programs selected. Once the device 20 has been configured for implementing the program 42 with compatibility with the server 12, the device 20, and any paired peripheral devices 49, may then be shipped to the user.

Next, at step 108, the user may activate the device 20 and optional peripheral devices 49. Activation of the device 20 may require the user to first verify their identity by responding to authentication information, such as by entering their date of birth. Upon correctly completing the authentication, at step 110, the user may immediately begin using the device 20, including the program 42.

At decision block 112, the process may determine whether data values associated with the program 42 meet a threshold, such as a minimum number of data values received or transferred within a given period of time. If the data values associated with the program 42 meet the threshold, the process continues to step 114 in which the server 12 updates user information, such as the EMR or Student Record in the first data structure 62. The server 12 may also provide updates to the device 20, including updates based on the data values received, such as updates to the program 42 and/or custom content 44, new programs 42 and/or custom content 44, an update to the firmware 24, an update to the device control module 48, an update to the sounds and/or appearance of the device 20, and so forth.

Next, at decision block 116, the process may determine whether the health plan, according to the program 42 or a predetermined timeframe by the provider, has been completed. If the health plan is not been completed, the process returns to step 110 in which the user continues to use the device 20, including the program 42. However, if the health plan has been completed, the process may continue, for example, to either of "Option 1" or "Option 2," among other others, for ending the program. For Option 1, at step 118, the server 12 sends a notification to the device 20, such as a visual alert (pop-up screen) displayed to the touchscreen interface, indicating the program has been completed and the device 20 must be returned within a specified period of time, preferably in a self-addressed postage paid package provided with the device 20 on initial delivery. Sometime thereafter, the server 12 may proceed to disable access to the device 20 by the user. Next, in step 120, the server 12 completely clears the device 20 of all content so that the device may be used by a next user without compromising any health or other personal information. The process then returns to step 102 in which the same device 20 may be configured in advance for the next user.

However, if upon the health plan being completed Option 2 is selected from decision block 116, the process may instead continue to step 122. At step 122, the server 12 sends a command to the device control module 48 to permanently deactivate so that the device control module 48 no longer controls aspects of the device 20 and no long responds to commands by the device manager 50. As a result, the server 12 ends control of the device 20, and ownership of the device 20 may be permanently transferred to the user thereby completing the reward for following the program.

Returning to decision block 112 in which the process determine whether data values associated with the program 42 meet a threshold, if the data values associated with the program 42 do not meet the threshold, the process may instead continue to step 124. At step 124, the server 12 may implement on action on the device, such as triggering an alert to the touchscreen interface, speakers, and/or vibration system. The process then continues to decision block 126 in which it is determined whether data values associated with the program 42 meet the threshold (similar to decision block 112). If the data values associated with the program 42 now meet the threshold, the process may return back to step 114 in which the server 12 may update user information and/or provide updates to the device 20. However, if the data values associated with the program 42 still do not meet the threshold, at decision block 128, the process may determine whether to try again based on the current state of the device 20. If the process determines to try again, the process may return to step 124 in which the server 12 may implement another action on the device, such as another triggering of an alert to the touchscreen interface, speakers, and/or vibration system. The process may continue in this looping fashion with configurable timing intervals until data values associated with the program 42 that meet the threshold are ultimately received. In addition, the process may change the action from one loop to the next, potentially with increasing severity in succeeding loops. For example, actions in the first several loops may provide only repetitive alerts to the touchscreen interface, whereas actions in later loops may add repetitive sounds to the speaker and/or repetitive vibrations. Actions in even later loops may take more sever actions, including disabling system applications 46 of the device 20, such as an Internet browser and games, disabling the first wireless communications interface 32 (cellular data interface) of the device 20 (or corresponding cellular data plan with the carrier), limiting the available data capacity for downloads, and so forth.

As a final resort, at decision block 128, the process may determine to no longer try again based on the current state of the device 20. The process may then continue to Option 1 at step 118, in which the server 12 sends a notification to the device 20, such as a visual alert (pop-up screen) displayed to the touchscreen interface, indicating the program has terminated and the device 20 must be returned within a specified period of time, followed by step 120 in which the server 12 completely clears the device 20 of all content.

Figure 3:
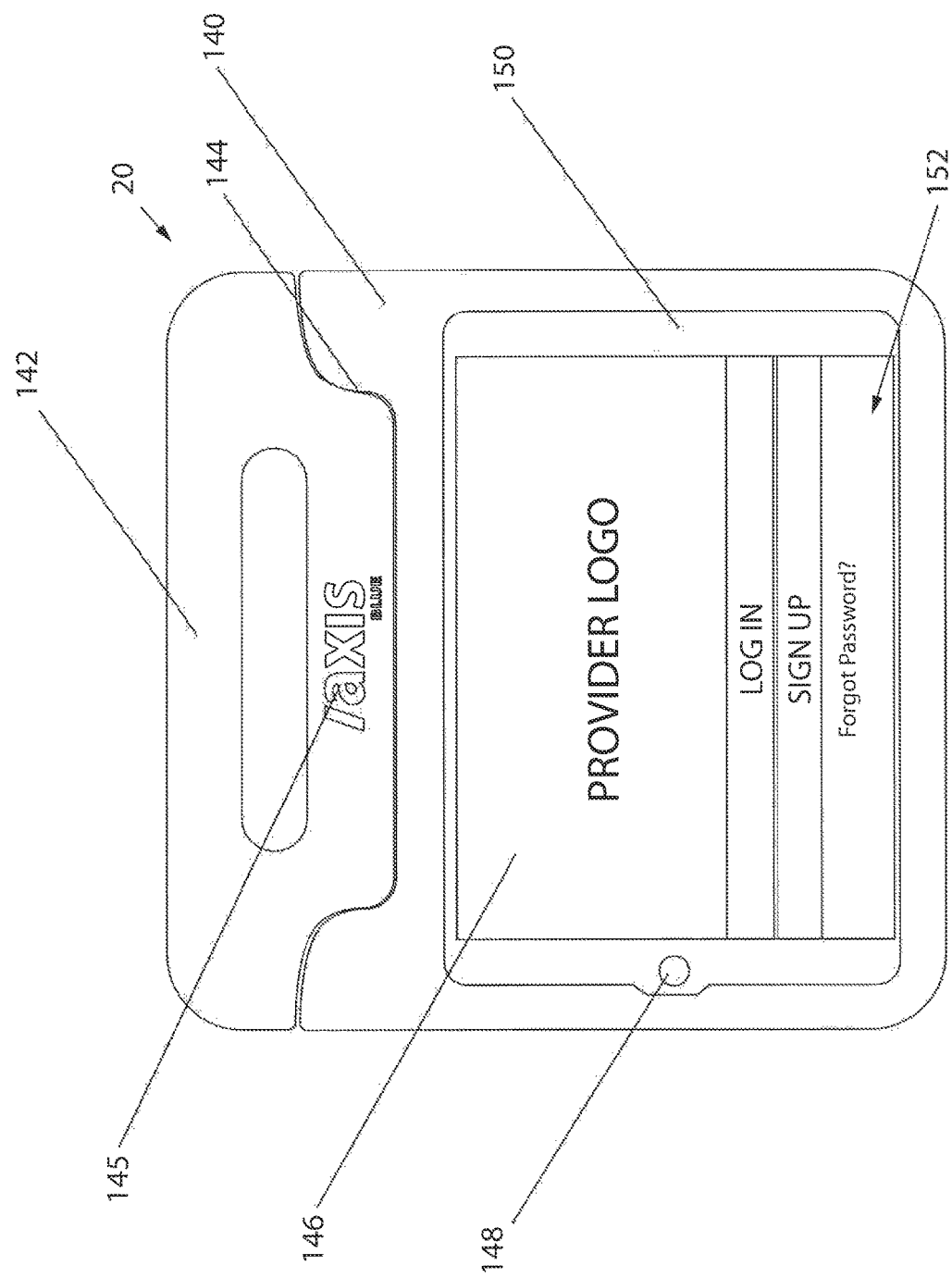
FIG. 3 is a portable electronic device which may be used in the system of FIG. 1.

Referring now to FIG. 3, a portable electronic device 20 is provided which may be used in the system of FIG. 1 in accordance with an embodiment of the invention. The device 20 may include a childproof, elder friendly, impact resistant durable case 140 which may be brightly colored and ergonomic in design for maximum ease of use by a user. The case 140 may include a handle portion 142 with ergonomic grip suitable for ease of carrying. In one aspect, the handle portion 142 may provide an integrated stand for attending live video sessions with health professionals. Accordingly, the handle portion 142 may rotate, for example, at pivot points 144 from a first position (as shown) that, is substantially flat with a touchscreen interface 146 of the device 20 to a second position (not shown) that is angled with respect to the touchscreen interface 146 for standing the device 20 upright. In addition, or alternatively, the device 20 may include clamps for a walker or treadmill. The case 140 may also include branding 145 for identifying a particular provider.

As may be seen in FIG. 3, the I/O system 26 includes the touchscreen interface 146 and a home button 148, and the sensors 28 may include a camera 150. The device 20 may include a default splash screen 152 displayed to the touchscreen interface 146 which may display a particular provider's logo, a prompt to log in, a prompt to sign up, and/or a prompt to recover a forgotten password.

Figure 4:
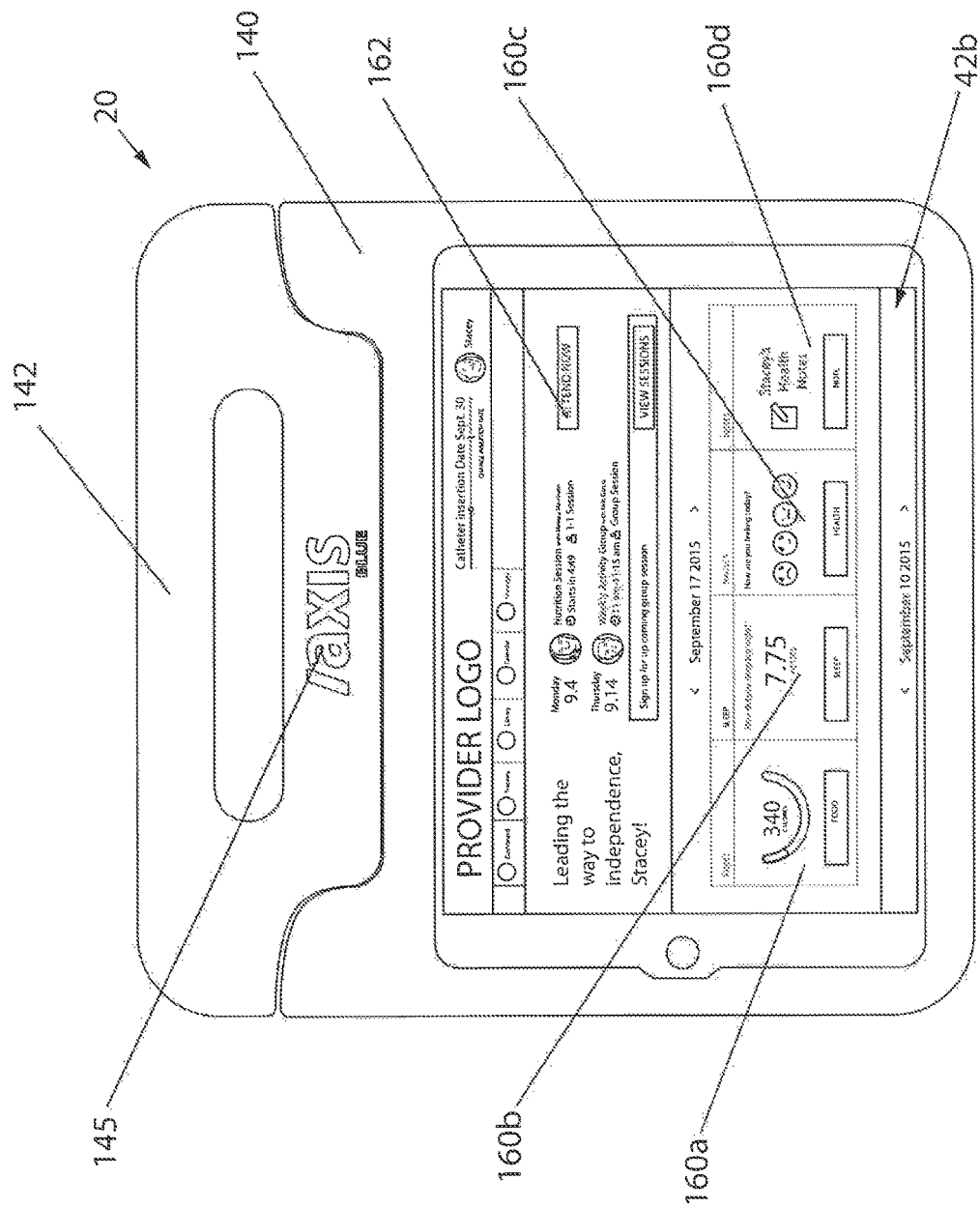
FIG. 4 is the portable electronic device of FIG. 3 in which the device is displaying a service program, which may be a health program, configured to receive data values in accordance with an embodiment of the invention.

Referring now to FIG. 4, the portable electronic device 20 may operate to display the program, such as the second program 42b (catheter health program), as illustrated in accordance with an embodiment of the invention. The second program 42b may have various data entry interfaces 160, such as: a first data entry interfaces 160a in which the user may enter data values corresponding to food consumption via the touchscreen interface 146; a second data entry interfaces 160b in which the user may enter data values corresponding to sleep via the touchscreen interface 146 and/or a peripheral device 49, such as a wearable activity tracker; a third data entry interfaces 160c in which the user may enter data values corresponding to a rated mood via the touchscreen interface 146; and/or a fourth data entry interfaces 160d in which the user may enter data values corresponding to the user's notes via the touchscreen interface 146; among others. In addition, the user may track other content, such as available video conferences, and may select a video conferencing icon 162 to join a live video conference. Entry of data values via the data entry interfaces 160 and/or transfer of content via the video conferencing icon 162 are illustrated as examples for data values which may be monitored by the server 12 and/or the device 20 for comparing to a threshold and implanting actions according to FIGS. 1 and 2 as described above.

Although the best mode contemplated by the inventors of carrying out the present invention is disclosed above, practice of the above invention is not limited thereto. It will be manifest that various additions, modifications and rearrangements of the features of the present invention may be made without deviating from the spirit and the scope of the underlying inventive concept.

What is claimed is:

1. A portable electronic device for running a service program, comprising:
   a wireless communications interface;
   a touchscreen interface; and
   a processor executing a program stored in a non-transient medium operable to:
   execute a first program being a service program configured to receive a plurality of data values from a user;
   communicate the plurality of data values to a server via the wireless communications interface; and
   execute a second program being a device control module configured to provide control over a function of the portable electronic device, the device control module being in communication with the server, wherein the device control module is configured to implement an action on the portable electronic device when the plurality of data values fails to meet a threshold, the action comprising disabling the user's access to the function of the portable electronic device.

2. The portable electronic of claim 1, wherein the wireless communications interface is a first wireless communications interface that is a cellular data interface, and further comprising a second wireless communications interface that is a wireless local area network (WLAN) interface, wherein the action is to disable the user's access to the cellular data interface.

3. The portable electronic of claim 2, further comprising a third wireless communications interface that is a Bluetooth interface, wherein the device is further operable to receive the plurality of data values via the Bluetooth interface.

4. The portable electronic of claim 1, wherein the device is further operable to execute a system application, and wherein the action is to disable the user's access to the system application.

5. The portable electronic of claim 4, wherein the system application is an Internet browser.

6. The portable electronic of claim 1, wherein the action further comprises to display a message to the touchscreen interface and to produce at least one of an audible alert and a vibratory alert.

7. A system for running a service program, comprising:
   a server having a server communications interface and a processor executing a program stored in a non-transient medium operable to execute a device manager; and
   a portable electronic device including:
   a wireless communications interface;
   a touchscreen interface; and
   a processor executing a program stored in a non-transient medium operable to:
   execute a first program being a service program configured to receive a plurality of data values from a user;
   communicate the plurality of data values to the server via the wireless communications interface; and
   execute a second program being a device control module configured to provide control over a function of the portable electronic device, the device control module being in communication with the device manager of the server, wherein the device control module is configured to implement an action on the portable electronic device upon receiving a command from the device manager, and wherein the device manager sends the command when the plurality of data values fails to meet a threshold, the action comprising disabling the user's access to the function of the portable electronic device.

8. The system of claim 7, wherein the wireless communications interface is a first wireless communications interface that is a cellular data interface, and further comprising a second wireless communications interface that is a wireless local area network (WLAN) interface, wherein the action is to disable the user's access to the cellular data interface.

9. The system of claim 8, further comprising a third wireless communications interface that is a Bluetooth interface, wherein the device is further operable to receive the plurality of data values via the Bluetooth interface.

10. The system of claim 9, further comprising a peripheral device configured to communicate with the portable electronic device via the Bluetooth interface, wherein the portable electronic device is further operable to receive the plurality of data values via the Bluetooth interface.

11. The system of claim 10, wherein the peripheral device is at least one of a wearable activity tracker and a glucose monitor.

12. A method for running a service program, comprising:
executing a first program being a service program on a portable electronic device, the portable electronic device comprising a wireless communications interface, a touchscreen interface and a processor executing a program stored in a non-transient medium, the service program receiving a plurality of data values from a user;
communicating the plurality of data values to a server via the wireless communications interface; and
executing a second program being a device control module on the portable electronic device, second program being configured to provide control over a function of the portable electronic device, the device control module being in communication with the server, the device control module implementing an action on the portable electronic device when the plurality of data values fails to meet a threshold, the action comprising disabling the user's access to the function of the portable electronic device.

13. The method of claim 12, wherein the wireless communications interface is a first wireless communications interface that is a cellular data interface, and further comprising a second wireless communications interface that is a wireless local area network (WLAN) interface, wherein the action comprises disabling the user's access to the cellular data interface.

14. The method of claim 13, further comprising a third wireless communications interface that is a Bluetooth interface and receiving the plurality of data values via the Bluetooth interface.

15. The method of claim 12, further comprising the device executing a system application, wherein the action comprises disabling the user's access to the system application.

16. The method of claim 15, wherein the system application is an Internet browser.

17. The method of claim 12, wherein the action further comprises displaying a message to the touchscreen interface and producing at least one of an audible alert and a vibratory alert.

* * * * *